United States Patent [19]

Ott

[11] Patent Number: 4,763,678
[45] Date of Patent: Aug. 16, 1988

[54] CLEANING APPARATUS FOR ELONGATED ENCLOSED CHANNEL DEVICES

[75] Inventor: Beverly J. Ott, Stewartville, Minn.

[73] Assignee: Mayo Medical Resources, Rochester, Minn.

[21] Appl. No.: 947,769

[22] Filed: Dec. 30, 1986

[51] Int. Cl.⁴ .............................................. B08B 3/04
[52] U.S. Cl. .................................. 134/171; 134/104; 134/166 C; 134/168 C; 134/169 C; 422/300; 422/301
[58] Field of Search ................... 134/14, 22.11, 22.12, 134/98, 99, 104, 166 C, 168 C, 169 C, 170, 171; 422/300, 301

[56] References Cited

U.S. PATENT DOCUMENTS

| | | | |
|---|---|---|---|
| 3,893,843 | 7/1975 | Fry et al. | 134/10 |
| 3,956,011 | 5/1976 | Carleton | 134/21 |
| 3,957,252 | 5/1976 | Storz | 259/1 R |
| 3,958,566 | 5/1976 | Furihata | 128/4 |
| 3,963,438 | 6/1976 | Banez | 21/58 |
| 3,980,078 | 9/1976 | Tominaga | 128/4 |
| 4,064,886 | 12/1977 | Heckele | 134/95 |
| 4,078,943 | 3/1978 | Saurenman | 134/14 |
| 4,190,041 | 2/1980 | Chikama | 128/4 |
| 4,216,767 | 8/1980 | Aoshiro | 128/6 |
| 4,278,101 | 7/1981 | Tanaka et al. | 134/167 C |
| 4,281,674 | 8/1981 | Tanaka et al. | 134/95 |
| 4,282,179 | 8/1981 | Gunther | 422/27 |
| 4,288,882 | 9/1981 | Takeuchi | 15/88 |
| 4,299,244 | 11/1981 | Hirai | 134/102 |
| 4,337,223 | 6/1982 | Kaye | 422/112 |
| 4,380,530 | 4/1983 | Kaye | 422/300 |
| 4,391,287 | 7/1983 | Konoshima | 134/99 |
| 4,410,492 | 10/1983 | Kaye | 422/27 |
| 4,447,399 | 5/1984 | Runnells et al. | 422/113 |
| 4,449,518 | 5/1984 | Konomura et al. | 128/4 |
| 4,473,921 | 10/1984 | Weber et al. | 15/304 |
| 4,489,741 | 12/1984 | Ogasawara | 134/179 |
| 4,525,220 | 6/1985 | Sasa et al. | 134/21 |
| 4,526,622 | 7/1985 | Takamura et al. | 134/21 |
| 4,526,623 | 7/1985 | Ishii et al. | 134/21 |
| 4,537,209 | 8/1985 | Sasa | 134/166 C |
| 4,576,650 | 3/1986 | Yabe et al. | 134/22.12 |
| 4,579,597 | 4/1986 | Sasa et al. | 134/21 |
| 4,579,598 | 4/1986 | Sasa et al. | 134/22.12 |

Primary Examiner—Harvey C. Hornsby
Assistant Examiner—Frankie L. Stinson
Attorney, Agent, or Firm—Kinney & Lange

[57] ABSTRACT

A cleaning system in which an elongated object having enclosed channels can be inserted in a rotatably mounted container in a tank to coil therein for cleaning by fluids pumped through the object and into the tank.

21 Claims, 9 Drawing Sheets

CLEANING APPARATUS FOR ELONGATED ENCLOSED CHANNEL DEVICES

BACKGROUND OF THE INVENTION

1. Field of the Invention

The present invention relates to the cleaning, including disinfecting and even sterilization, of elongated enclosed channel devices and, more particularly, to such cleaning of endoscopes after use in a biological organism, typically the human body.

Endoscopes are protectively encased bundles of flexible optical fibers used to transmit images to the operator at one end from otherwise inaccessible regions into which the opposite end of the instrument is inserted to thereby obtain a view of the structures about such regions Such an arrangement makes possible the visual examination, and even photographing, of structures surrounding cavities to which there is some some external access, such access usually being a relatively small opening and which often extends a considerable distance from the cavity of interest. Typically, such cavities in the human body are formed by the structures of one or more internal organs thereabout and to which there is some access through a bodily orifice.

Not only can an endoscope be inserted through such an orifice into such a bodily cavity and manipulated to permit viewing in different directions therein, but also such instruments are usually built with means to permit the insertion of fluids into such cavities. Often, there are also means for the removal of tissue from portions of the surrounding organ structures. Thus, in addition to the fiber optic bundle, there is usually provided a plurality of enclosed channels or passageways more or less paralleling the direction of the fiber optic bundle which are formed also within the enclosure protecting the fiber optic bundle. Specifically, such channels are typically provided to carry one or more of water, air and carbon dioxide gas. A further channel is often provided to permit the instrumentation to extend therethrough necessary for a biopsy to extract cellular tissue or other matter from the cavity being viewed or from the structure surrounding such cavity. This latter channel may also be connected to a vacuum source as a means of obtaining sample fluids, for instance.

Figure 1:
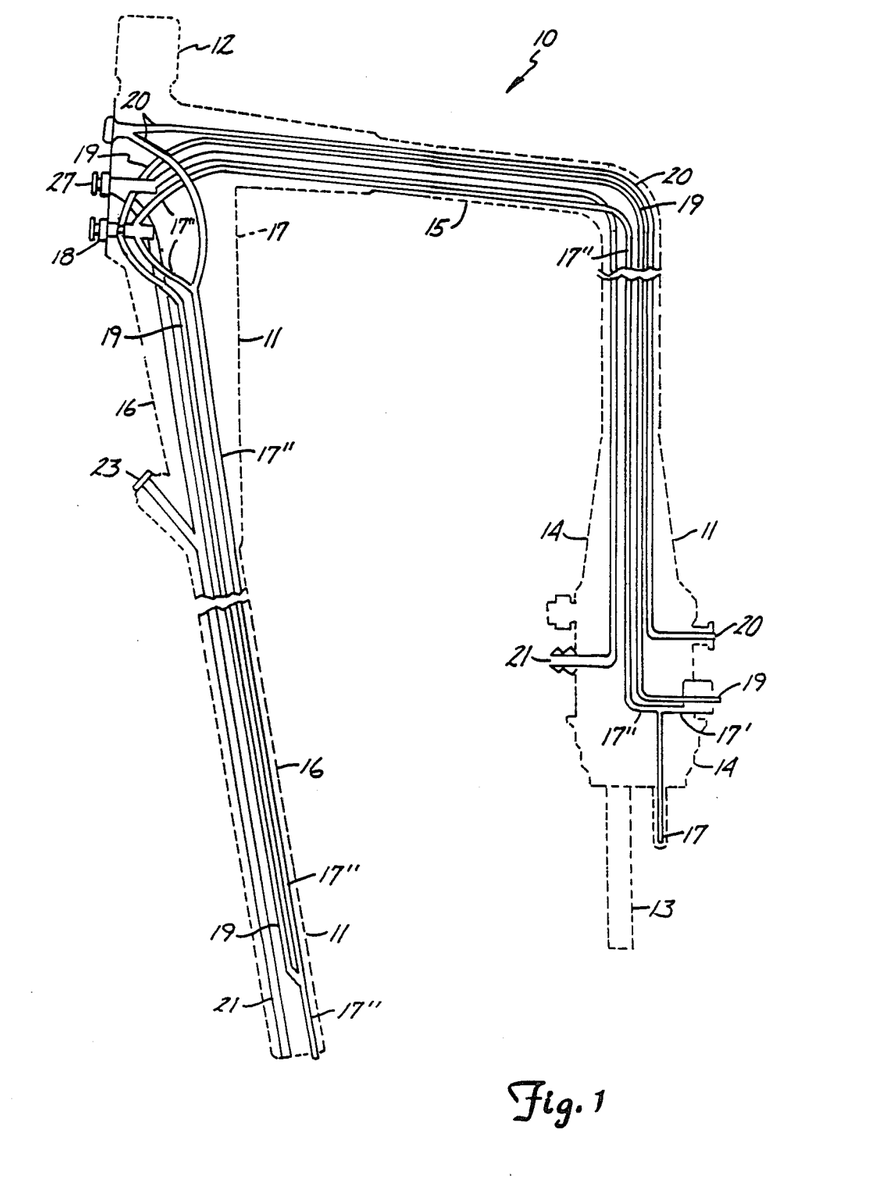
FIG. 1 shows a diagram of a representative endoscope.

FIG. 1 shows a representation of a structure for a typical endoscope, 10, although not necessarily the replica of any particular currently available endoscope. Endoscope 10 has a protective outer jacket, 11, shown in dashed line form. There is a viewing eyepiece, 12, and a light source connector, 13, as interfaces for providing useful access to the fiber optic bundle in endoscope 10 but which is not shown in FIG. 1. Shown in FIG. 1, however, in solid lines, are several of the passageways or channels just referred to. These passageways begin in a primary interface portion, 14, of endoscope 10. They continue through the operation portion, 15, and down into the insertion portion, 16.

The first channel or passageway to be considered, 17, begins at an access orifice at the end in primary interface portion 14. This orifice is intended to receive pressurized air which can then flow to two regions, the first being a water reservoir portion along passageway, 17'. Air flowing along passageway 17' is intended to flow into a water reservoir (not shown) to provide pressure to pressurize the water therein. The other direction of air flow is along passageway, 17'', through primary interface portion 14, and into control portion 15 where the flow is controlled by a valve means, 18. From there passage 17' continues through the remainder of control portion 15 and into insert portion 16 where it terminates at a termination orifice at the end of insertion portion 16.

A second channel or passageway, 19, again has an access orifice in primary interface portion 14 where it is adapted to be connected to the same water reservoir as is passageway 17'. Thus, pressurized air along passageway 17' provides the force to move water from such a reservoir along passageway 19 through primary interface portion 14 to control portion 15 and valve 18, which also controls water flow. From valve 18, passageway 19 continues through insertion portion 16 where it merges into passageway 17'' to end at the termination orifice thereof.

A further passageway, 20, for carbon dioxide gas also has its access orifice in primary interface portion 14. Passageway 20 continues through primary interface portion 14 into control portion 15 where it merges with passageway 17'' to thereby reach insertion portion 16 and the corresponding termination orifice.

The last passageway, which once again has its access orifice in primary interface portion 14, is the passageway designated 21 which is adapted for connection to a source of vacuum. Passageway 21 continues through primary interface portion 14 and into control portion 15 where it meets with a valve, 22, to control flow therethrough. Thereafter, passageway 21 continues through the remainder of control portion 15 and into insert portion 16 where it reaches a termination orifice. However, there is a further access port, 23, provided in control portion 15 to passageway 21 to permit insertion of those instruments needed for biopsies and the like.

Endoscopes currently available have differing designs and capabilities in being different in length, number of channels or passageways, and the like. However, most will have a structure which will reflect in some degree that shown in FIG. 1, although the merging of channels may occur at different points or there may be other structural differences from the structure shown.

Nevertheless, most of them, in having some aspects in common with the structure shown in FIG. 1, will be subject to blockages or contamination because of biological matter coming to reside in the channels or passageways, having found its way in there during use of the endoscope in a procedure within a bodily cavity. Thus, there is a need for an apparatus to clean various differing kinds of endoscopes, apparatus which cleans each of the channels or passageways therein as well as the exterior surface thereof to the point of disinfecting. Such a cleaning apparatus should permit this kind of cleaning of all of the channels simultaneously to speed the cleaning process, and should permit viewing the channel orifices to see that cleaning fluid flow is occurring therethrough. Further, the use of a disinfectant fluid should be dynamic with respect to the endoscope being cleaned and flow during the procedure to assure disinfectant continually being provided to the surfaces being cleaned. Static disinfectant fluid may lead to hardening biological matter in place in a passageway.

SUMMARY OF THE INVENTION

The present invention provides a cleaning system having an insertion tank in which an elongated object having enclosed channels can be inserted to reach a container rotatably mounted in such an insertion tank so that the object can bend around in said container to coil up therein with a remaining portion of the object outside of the tank. This outside remaining portion is where an access connection is made by the cleaning system to permit cleaning fluid to flow through all of the channels and into the insertion tank. Cleaning fluid flow is controlled by a valve to determine the flow through the object, and a further valve to determine filling of the insertion tank by means other than through the object. Overflow connections to the insertion tank permit a continuous flow of cleaning fluids through the object channels and the insertion tank.

DETAILED DESCRIPTION OF THE PREFERRED EMBODIMENTS

Figure 2:
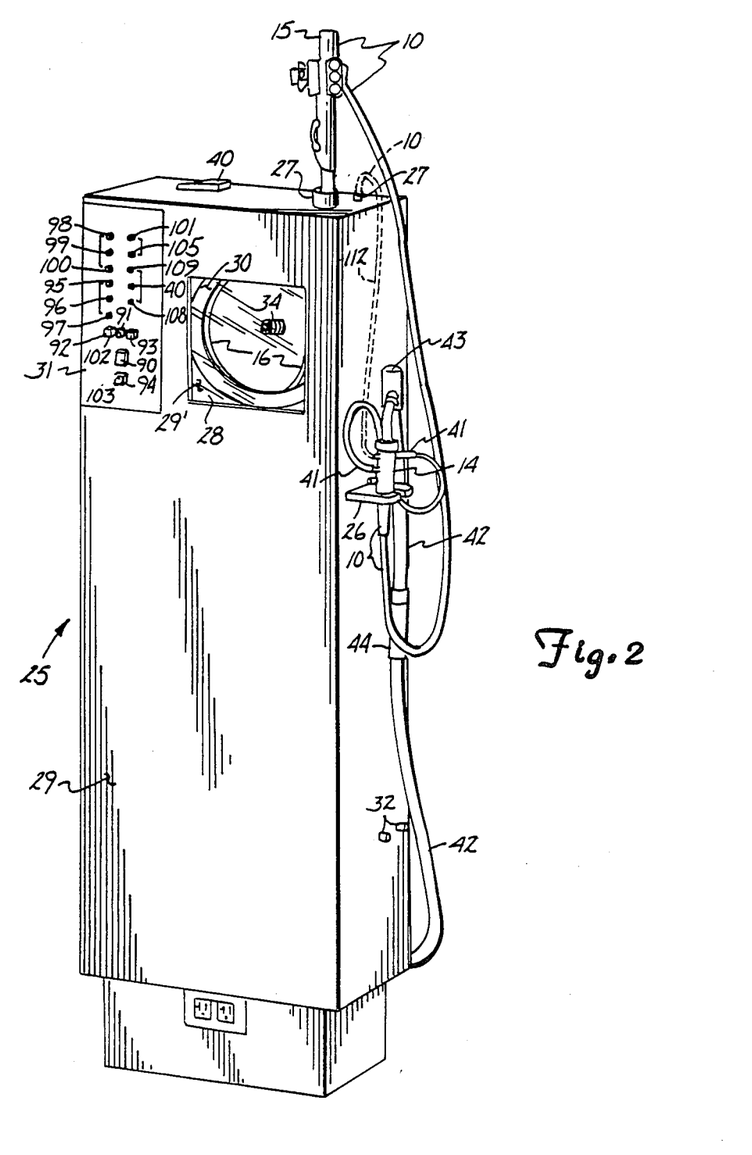
FIG. 2 shows a front view of the present invention.

FIG. 2 shows a front view of a cleaning system, 25, with endoscope 10 of FIG. 1 in place in system 25 for cleaning, including disinfecting and rinsing. Endoscope 10 has its primary interface portion 14 held by a support, 26. Control portion 15 of endoscope 10 can be seen to be above an endoscope cleaning insertion opening, 27, through which insertion portion 16 of endoscope 10 has been inserted to be within a transparent insertion tank, 28.

Insertion tank 28 can be seen at the front, 29, of cleaning system 25 through a viewing window, 29'. Much of insertion portion 16 of endoscope 10 is shown within a container, 30, located in insertion tank 28 and rotatably mounted therein, as can be more fully seen in FIGS. 3 and 4.

A control and information display panel, 31, is provided in front 29, as shown in FIG. 2. Connections, 32, for being joined with external fluid sources, are shown on the side of cleaning system 25. A power connection cord for connecting to alternating voltage electrical power is provided also, though not visible in FIG. 2.

Figures 3, 4:
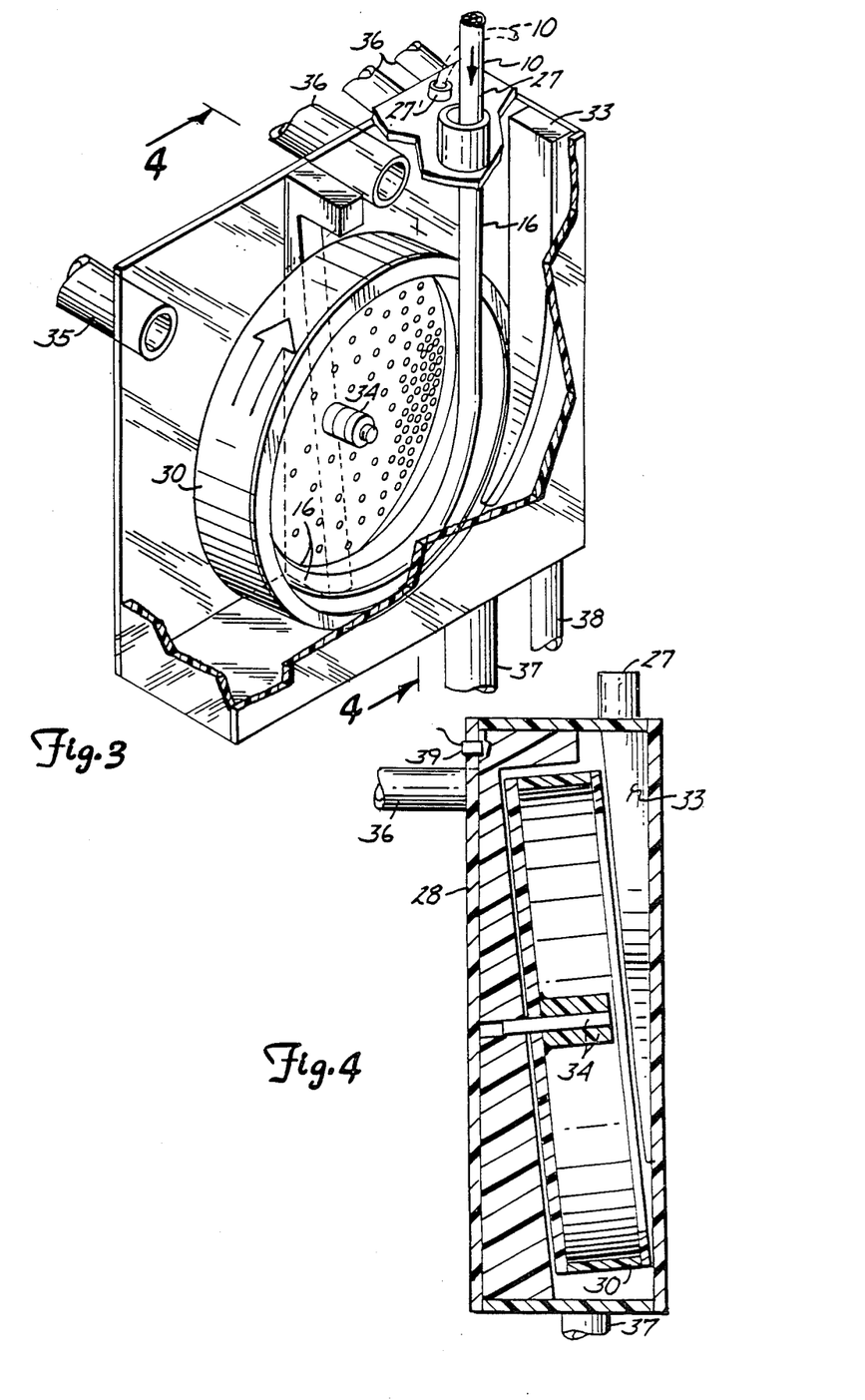
FIGS. 3 and 4 show alternative views of a portion of the present invention.

FIG. 3 shows insertion tank 28 with a portion of the transparent plastic walls of the tank broken away to more fully show circular cylinder shaped container 30 with insertion portion 16 of endoscope 10 contained therein. A guide, 33, aids in directing the end of insertion section 16 into an open end or circular side of container 30. Container 30 is mounted in insertion tank 28 by a rotary mount means, 34, on the end or circular side thereof opposite the open side used for receiving endoscope insertion portion 16. Rotary mount 34 permits container 30 to rotate in tank 28 in the presence of cleaning fluids in the tank, including commonly used disinfectants for endoscopes, even after being repeatedly submerged therein in repeated cleaning procedures. Such rotary mounts are well known and commercially available.

FIG. 4 is a cross section view of FIG. 3, as indicated in FIG. 3, and shows that container 30 is mounted on rotary mount 34 at an angle with respect to the vertical direction. As a result, insertion of insertion portion 16 of endoscope 10 through insertion opening 27, guided by guide 33, results in insertion portion 16 encountering the lowest positioned cylindrical side portion of container 30. There, container 30, in response to the insertion forces applied to endoscope 10 in placing it in tank 28, rotates to take up insertion portion 16 as it is continually pushed through insertion opening 27 into container 30. That is, each further part of insertion portion 16 reaching container 30 encounters and lays against the cylindrical sides of container 30 without significant sliding and abrading, and the first portion of insertion portion 16 also lays against the closed end or circular side of it supported by rotary mount 34. Rotation of container 30 causes insertion portion 16 to be taken up by container 30, becoming coiled against the cylindrical sides thereof, thus permitting both longer and shorter endoscopes to be completely contained within container 30 and insertion tank 28. Hence, a variety of endoscope insertion portion lengths can be accommodated in insertion tank 28.

Further shown in connection with insertion tank 28 is a disinfectant fluid overflow tube or pipe, 35. There are also shown rinse fluid overflow tubes or pipes, 36. At the botton of tank 28 are shown a drain tube or pipe, 37, and disinfectant and rinse fluids fill tube or pipe, 38. Note that tubes 36 are a bit higher in tank 28 than is tube 35, that is tubes 36 are a greater vertical distance above drain tube 37 than is tube 35.

Finally, a liquid level senser, 39, is shown at the top of tank 28 in FIG. 4 to indicate when fluid levels in tank 28 reach this point or depth, with the sensor electrical interconnection shown in part extending therefrom. Tank 28 might typically be designed to hold one and three-quarter gallons of liquid, but could be greater or smaller if desired.

Returning to FIG. 2, a latch, 40, holds closed a cover over the top of cleaning system 25. Latch 40 can be opened and the cover thereafter opened to remove tank 28 for cleaning purposes. This is easily done, but the various connected tubes described above must be disconnected to permit such removal.

Small tubes, 41, lead from cleaning system 25 and are connected to the access orifices of primary interface portion 14 of endoscope 10. Tubes 41 permit cleaning fluid flows through the passageways of endoscope 10 from cleaning system 25, which flows pass to insertion tank 28 from the termination orifices in insertion portion 16.

Further shown in FIG. 2 is a system drain pipe or tube, 42, which has an upper connection, 43, to cleaning system 25 and a lower connection, 44, to cleaning system 25. The lower unseen end of drain tube 42 is to be connected to a waste gathering or disposal means or sewer which is at a lower elevation than is connection 44 to be certain that gravity assists draining from cleaning system 25 through tube 42.

Figure 5:
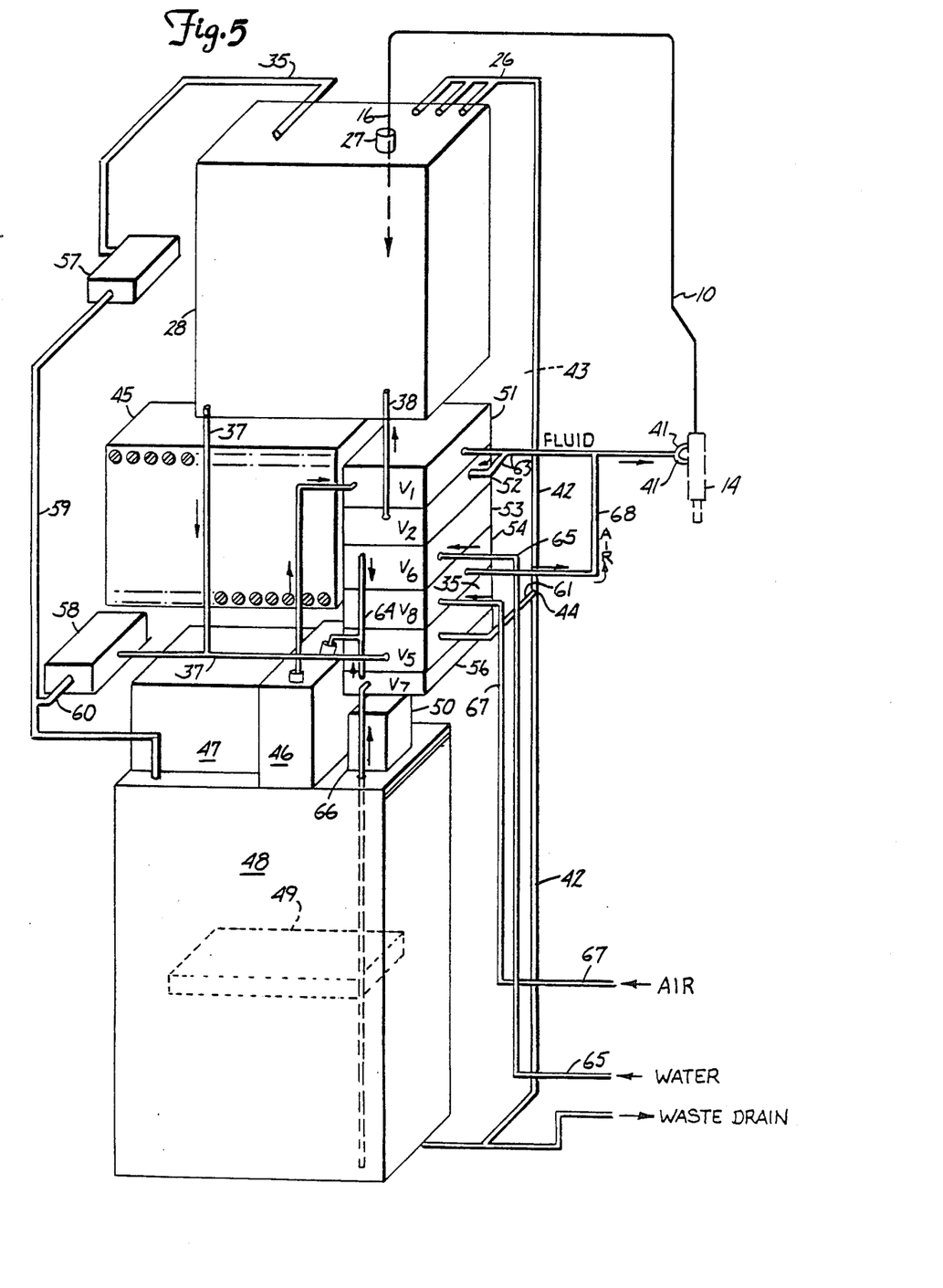
FIGS. 5 and 6 are diagrams of the various cleaning fluid flow paths, the components therealong and the controls therefore.

FIG. 5 shows in diagrammatic form the structural arrangement occurring inside of cleaning system 25. The components represented in FIG. 5 carry the same designations as those components do in the other figures. Insertion tank 28 is shown in a representational sketch with endoscope 10 represented as having its insertion portion inserted in insertion opening 27. Tubes 41 are shown connected to the primary interface portion 14 of endoscope 10.

Further components represented are an industrial programmable controller or control computer, 45, commercially available from Texas Instruments, Inc., under the designation TI 140, which provides timing signals selected by the user to certain system components to control operation of cleaning system 25. Such signal selection can be accomplished in a well known manner such as by placing a corresponding pattern in a commercially available read-only memory.

A pump, 46, is driven by a motor, 47. These are shown on top of a compartment containing a reservoir, 48, which has adjacent to it a heating means, 49, for heating the reservoir fluid to a selected temperature. A disinfectant in reservoir 48 sufficiently heated can provide a sterilizing fluid. Heating means 49 is controlled by a heating controller, 50. There is further shown a plurality of valves which control fluid flow therethrough between the input and output of the valve. The valves are designated 51 through 58.

Figure 6:
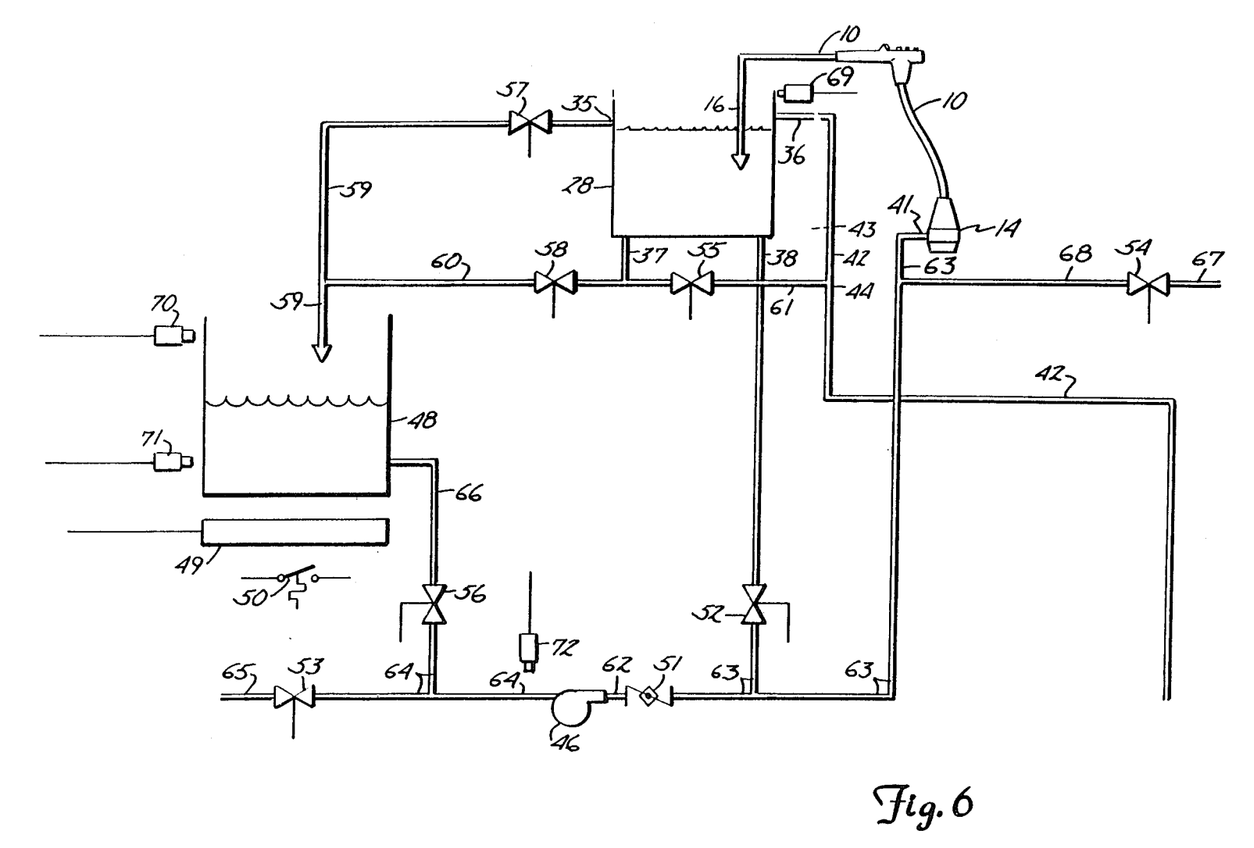

These various components are interconnected by tubes or pipes or by electrical interconnections, or by both. FIG. 5 shows in one diagrammatic form the piping or tubing interconnections which are shown again in another diagrammatic form in FIG. 6. Again, the numerical designations given in FIG. 6 are those given for the actual components in other figures or in the diagrammatic representation of those components in other figures.

Overflow tube 35 from insertion tank 28 is connected to the input of electrically controlled solenoid valve, 57. A tube, 59, is connected to the output of valve 57 and made accessible to reservoir 48 at a first fill opening thereof. Insertion tank drain tube 37 is connected to the input of electrically controlled solenoid valve 58. The output of valve 58 is connected by a tube, 60, to tube 59. Drain tube 37 is also connected to the input of electrically controlled solenoid valve 55. The output of valve 55 is connected by a tube, 61, to cleaning system 25 drain tube 42 at junction 44, as is shown on the outside of cleaning system 25 in FIG. 2.

Pump 46 is connected by a tube, 62, to the input of ball check valve 51. The output of valve 51 is connected by a tube, 63, to tubes 41 and to the input of an electrically controlled solenoid valve 52. The output of valve 52 is connected by fill tube 38 to insertion tank 28. Pump 46 has its input supplied by tube, 64. Tube 64 leads to pump 46 from the output of electrically controlled solenoid valve 53 and from the output of electrically controlled solenoid valve 56. Valve 53 has its input connected by a tube, 65, to a source of water, typically the water supply provided in the building of the user. Valve 56 has its input connected by a tube, 66, connected to reservoir 48.

Electrically controlled solenoid valve 54 has its input connected by a tube, 67, to a source of compressed air. The output of valve 54 is connected by a tube, 68, to tube 63 and then to tubes 41.

As earlier indicated, operation of cleaning system 25 is controlled by programmable controller 45 which does so by directing the operation of the various solenoid valves, and of pump 46 and motor 47, while obtaining information from various sensors. FIG. 6 shows a representation of a sensor, 69, which senses the occurrence of a liquid level at the top of insertion tank 28 past the overflow tubes 35 and 36. This level could be reached only because of a blockage somewhere in the system in the paths leading from these tubes. A further pair of sensors, 70 and 71, represented in FIG. 6, are used to sense certain liquid levels in reservoir 48, with sensor 71 sensing whether the liquid level is too low and sensor 70 sensing whether such level is too high. Thus, imminent overflow or insufficient fluid quantities can be sensed and reported by controller 45 to the cleaning system operator.

Finally, a liquid presence sensor, 72, is represented in FIG. 6 and ascertains whether there is liquid available at pump 46 to be drawn therethrough to prevent pump 46 from being damaged by the absence of such a fluid in it not being present at the pump input for pumping. Reservoir 48 typically contains on the order of four and one-half gallons of a liquid disinfectant compatible with endoscopes. This disinfectant might typically be a 2% water based solution of glutaraldehyde. This disinfectant type and others are commecially available and compatible with the material used in endoscopes. The tubes, valves and the like used in cleaning system 25, of course, are also chosen to be compatible with the commercially available disinfectants usable with endoscopes.

Figure 7:
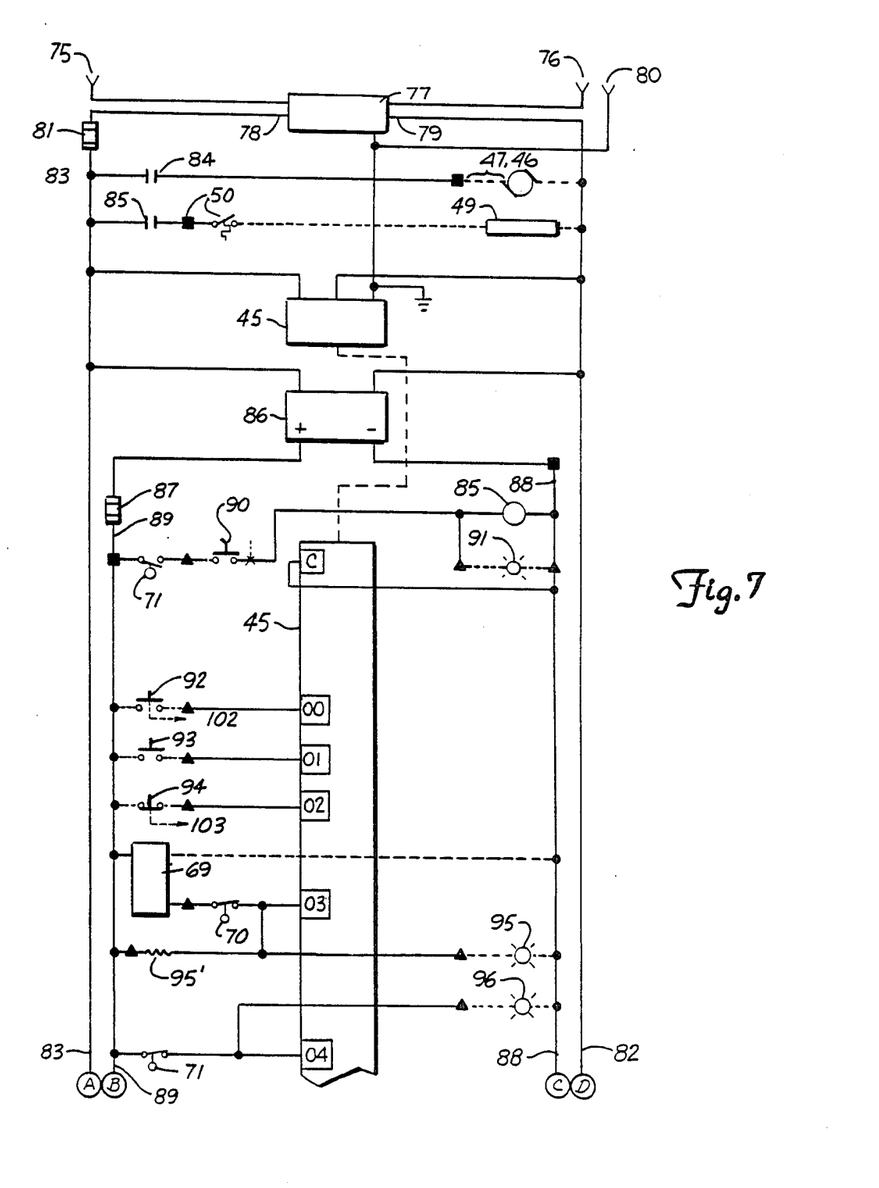
FIGS. 7, 8 and 9 show electrical schematic diagrams of the circuits used in the present invention.
Figure 8:
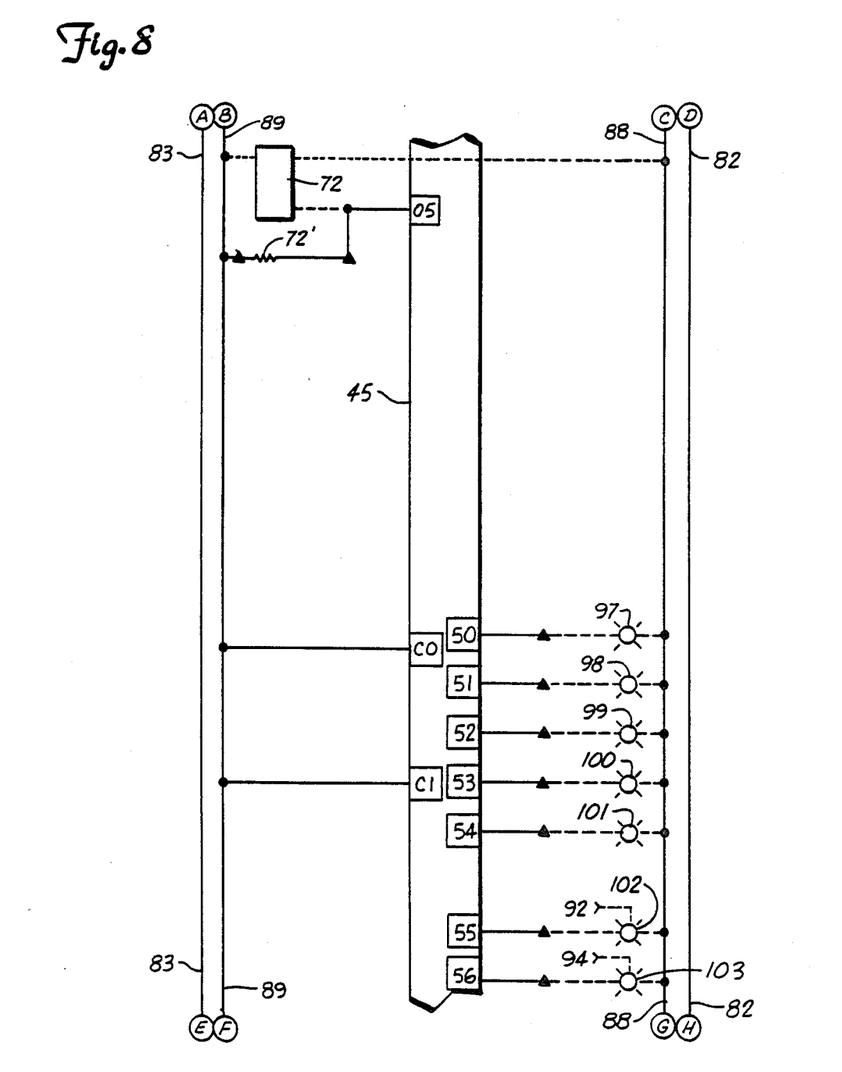
Figure 9:
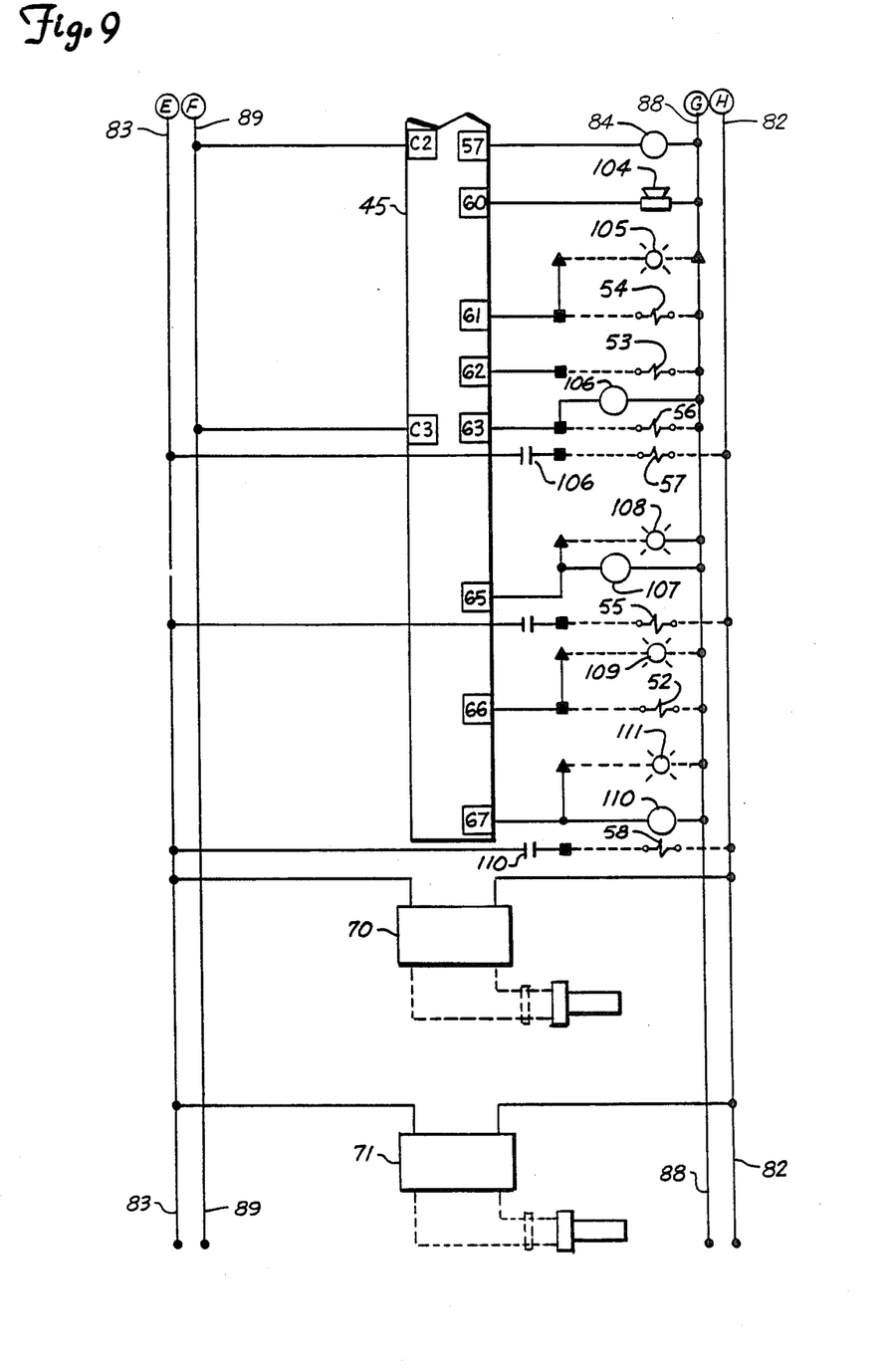

FIGS. 7, 8 and 9 show the electrical interconnection arrangement used for cleaning system 25. An external alternating voltage source providing nominally 120 V at 60 Hz is to be connected between terminals 75 and 76 in FIG. 7 with terminal 76 being connected to the common side of this source. This voltage is supplied to a ground fault interrupter, 77, which voltage is provided through interrupter 77 to terminals 78 and 79 for energizing the remaining portions of the system. An external ground, 80, is also connected to ground fault interrupter 77. A 12 amp fuse, 81, is used to protect cleaning system 25. Thus, alternating voltage for operation of the remaining devices in cleaning system 25, exclusive of the protective devices just mentioned, is provided between a common line, 82, and a "hot" line, 83.

First connected between protected alternating voltage interconnection lines 82 and 83 is pump motor 47 and pump 46 under control of a solid state relay, 84, having its actuation side connected in series therewith. The dark square represents a terminal on a control circuit board.

Next connected between interconnection power lines 82 and 83 is heater 49 and heat controller 50, including a thermostatic switch operated by the temperature sensed for reservoir 48. This heating arrangement is also under control of a relay, 85, having its actuation side in series therewith. Alternating voltage is then shown provided to programmable controller 45, and then to a direct voltage power supply, 86, which provides a direct voltage of 24 V. The relatively positive polarity side of supply 86 is connected to another fuse, 87, of a 2 amp value. Thus, a direct voltage of 24 V is supplied between lines 88 and 89 with the relatively negative side connected to interconnection line 88 and the relatively positive side connected to line 89.

First connected between the direct voltage interconnection lines 88 and 89 is a switch controlled by low liquid sensor 71 at reservoir 48 in series with a temperature on/off switch, 90. These two switches are in series with a parallel combination of the control side of solid state relay 85 and a "temperature on" indicator light, 91. Thus, the actuator side of solid state relay 85, shown near the top of FIG. 7 with heater 49, is operated by the control side of relay 85 under control of switches 71 and 90. The dark triangles represent connections to control panel 31 of FIG. 2. Indicator light 91, also shown in FIG. 2, then will be on, and heater 49 will be on if the thermostat temperature is not exceeded, upon the pushing of switch 90 to a closed position if there is sufficient liquid in reservoir 48 to cause switch 71 to be closed.

Next down in FIG. 7, shown in the central portion thereof, is a representation of terminal strips from programmable controller 45 as indicated by a dashed line joining these two items in that figure. The designations along the terminal strip portion representation of programmable controller 45 are those used in that device. The first connection is a common connection made from the device terminal designated C to relatively negative direct voltage line 88.

The next connection shown in FIG. 7 is of start switch, 92, made between interconnection power supply line 89 and terminal 00 in controller 45. This switch has a light therein which is illuminated when the switch is closed, as shown by dashed line arrow leading to a light, 102, in FIG. 8. Start switch 92 is used to start a cleaning procedure or to resume such a procedure that has been temporarily stopped by use of the later described stop button or because of an improper liquid level in reservoir 48.

The next item shown connected in FIG. 7 is a reset switch, 93, shown connected between power line 89 and terminal 01 in controller 45. Reset switch 93 can be used to begin a termination procedure after a cleaning procedure has begun and is in progress, or after a cleaning procedure has begun but has been temporarily stopped by the pushing of the stop button. The closure of switch 93 will begin a drain procedure to drain insertion tank 28. If a cleaning procedure was under way using a disinfectant fluid or was temporarily halted, the draining of insertion tank 28 will be to reservoir 48 through tube 37, valve 58, tube 60 and a portion of tube 59. On the other hand, if a rinsing fluid portion of the procedure was in progress or temporarily halted, closure of switch 93 will drain insertion tank 28 to the external waste drain arrangement through tube 37, valve 55, tube 60, connection 44, and cleaning system drain tube 42.

The next connection shown in FIG. 7 is of the stop switch or emergency stop switch, 94, shown connected between interconnection line 89 and controller terminal 02. Further, pushing the stop button to open switch 94 will cause a light in that switch to illuminate, as indicated by the dashed line arrow going to a light, 103, in FIG. 8. Stop switch 94 can be used to halt or temporarily halt any cleaning operation which is in progress at the time this switch is opened. As indicated previously, continuation of the cleaning procedure is caused by pushing the start switch 92 while an entirely new cleaning procedure is initiated by pushing reset switch 93.

The next items shown connected in FIG. 7 are high liquid level sensor 69 for checking on the liquid level in insertion tank 28 and a switch controlled by high liquid level sensor 70 checking on the liquid level in reservoir 48. Sensor 69 is shown connected between direct voltage lines 89 and 88 to receive direct voltage for operating this sensor. A switch controlled by sensor 69 is in series with a switch controlled by sensor 70 for connection to terminal 03 of controller 45. If either of these switches opens, controller 45 will terminate all operation of cleaning system 25 then in progress. This arrangement is also used to control the reservoir high level warning light, 95, which is connected in series with a 1000 value resistor, 95', capable of dissipating one watt. The opening of either of switches 69 or 70 will remove a short circuit across lamp 95 permitting that lamp to illuminate on panel 31 until the liquid levels are proper in both reservoir 48 and insertion tank 28.

The last connection shown in FIG. 7 has another switch controlled by low liquid level sensor 71 used with reservoir 48 and which is connected between interconnection line 89 and controller terminal 04. If switch 71 opens, controller 45 will stop any procedure in progress in cleaning system 25 at the time of such opening. Further, switch 71 controls a low level warning light, 96. The opening of switch 71 will lead to the illuminating of lamp 96 on panel 31.

The first item shown connected in FIG. 8 is "presence at pump of liquid" sensor 72 which is shown connected between direct voltage power lines 89 and 88 to provide power for opeating the sensor. Sensor 72 controls a switch which is connected between terminal 05 of controller 45 and a 1000, one watt resistor, 72', connected thereto which is also connected to line 89. Sensor 72 indicating the absence of liquid at pump 46 for pumping leads to voltage from line 89 being applied to controller 45 terminal 05 to stop any procedure in cleaning system 25 in progress at the time of such a sensing.

Two connections to line 89 are made at terminals C0 and C1 of controller 45 for obtaining positive direct voltage. Also shown in the remainder of FIG. 8 are the connections of several indicator and alarm lights controlled by controller 45. The first of these lights, 97, is a reservoir 48 "disinfectant supply time for change" alarm connected between power line 88 and terminal 50 of controller 45. Controller 45 keeps track of the number of cleaning cycles performed with a given batch of disinfectant and, after a preset number of same have occurred, provides an alarm indication by illuminating light 97 on panel 31.

The next light, 98, is for indicating that the disinfecting portion of the cleaning procedure is under way. Light 98 is connected between interconnection power line 88 and terminal 51 of controller 45.

The next two lights, 99 and 100, are for indicating on panel 31 that one or the other of the first and second rinsing portions of the cleaning procedure, respectively, are under way. Light 99 is connected between power line 88 and terminal 52 of controller 45. Light 100 is connected between line 88 and terminal 53 of controller 45.

A further light, 101, is for indicating on panel 31, during the disinfecting portion and the rinsing portion of a cleaning procedure, when the cleaning fluid used in those poritons is being forced through the channels or passageways of endoscope 10. Light 101 is connected between power line 88 and terminal 54 of controller 45.

The next two lights, 102 and 103, are the two earlier mentioned lights in the switch buttons for start switch 92 and stop switch 94, respectively. Light 102 is connected between line 88 and terminal 55 of controller 45. Light 103 is connected between power line 88 and terminal 56 of controller 45. These lights are illuminated on panel 31 when the corresponding switches 92 and 94 are closed, as indicated above.

Turning to FIG. 9, there are first shown two electrical power connections for controller 45. One is made between line 89 and terminal C2 of controller 45, and the other is made between line 89 and terminal C3 of controller 45.

The control side of solid state relay 84 for controlling pump 46 and pump motor 47 is then shown connected between power line 88 and terminal 57 of controller 45. Thus, power to pump 46 and pump motor 47 is switched on to cause pumping of liquids available thereto by signals generated in controller 45 directed through the control side of relay 84 to close the contacts on the actuator side of relay 84 shown toward the top of FIG. 7.

An audible alarm device, 104, sounds any time that any of the liquid level sensors on reservoir 48 and insertion tank 28 sense an undesirable liquid level. Audible alarm 104 is connected between power line 88 and terminal 60 of controller 45.

Next shown in FIG. 9 is the solenoid coil for solenoid valve 54 which is shown connected between power line 88 and terminal 61 of controller 45. Through this arrangement, controller 45 can permit compressed air to flow through tube 67, valve 54, tube 68 and a portion of tube 43 to tubes 41 and endoscope 10. A further light, 105, is connected in parallel with the solenoid coil fo valve 54 so that it is illuminated on panel 31 when valve 54 is opened. This indicates when, in the disinfecting and rinsing portions of a cleaning procedure, air is being forced through the channels or passageways of endoscope 10 to remove disinfectant residue or rinse residue and to dry, to some extent, these channels or passageways and thus further clear them.

The next connection shown in FIG. 9 is the solenoid coil for valve 53 connected between power line 88 and terminal 62 of controller 45. In this arrangement, controller 45 can cause valve 53 to open permitting water under pressure to flow through tube 65, valve 53 and tube 64 to reach pump 46. This water will then flow past pump 46, without its being operated, and ball check valve 51 to reach valve 52 through tube 63 and to reach endoscope 10 through tubes 63 and 41. From there, the water passes through the passageways of endoscope 10 to insertion tank 28.

There follows a connection between interconnection power line 88 and terminal 63 of controller 45 of the solenoid coil for valve 56 in parallel with the control side of a relay, 106. The actuator side of relay 106 is in the connection next shown therebelow which is in series with the solenoid valve for valve 57 between alternating voltage lines 82 and 83. In this arrangement, controller 45 permits disinfectant fluid from reservoir 48 to travel along tube 66, through valve 56 and along tube 64 to reach pump 46. The operation of pump 46 is then required for this fluid to reach valve 52 and endoscope 10. At the same time, whenever valve 56 is opened, relay 106 is also actuated at its control side to cause its actuator side to close permitting electrical power to energize the solenoid coil of valve 57. As a result, the release of disinfectant fluid from reservoir 48 to pump 46 is always accompanied by permitting a flow out of insertion tank 28 through tube 35, valve 57 and tube 59 back to reservoir 48. Thus, controller 45 can direct a continual disinfectant flow forced by pump 46 through endoscope 10 and through insertion tank 28 with the assurance that tank 28 will not fill past the level of tube 35 unless some tube blockage ensues. That is, a continuous disinfectant flow through and around endoscope 10 is provided.

Another control side of a relay, 107, is shown as the next connection in FIG. 9 between interconnection power line 88 and terminal 65 of controller 45. The actuator side of relay 107 is shown just therebelow in series with the solenoid coil of valve 55 which together are between alternating voltage interconnection lines 82 and 83. This connection permits controller 45 to drain insertion tank 28 through tube 37, valve 55, connection 44 and into cleaning system drain line 42. An indicator light, 108, is in parallel with the control side of relay 107 so that this light will be illuminated on panel 31 when valve 55 is opened.

The filling of insertion tank 28 directly rather than through endoscope 10 is controlled by valve 52 which has its solenoid coil next connected in FIG. 9 between interconnection power line 88 and terminal 66 of controller 45. A further light, 109, is in parallel with the solenoid coil of valve 52 so that this light is illuminated on panel 31 whenever valve 52 is opened to permit pump 46 to pump a fluid into insertion tank 28 to aid in the cleaning or flushing of the exterior of endoscope 10.

The final valve control shown in FIG. 9 is based on having the control side of a further relay, 110, connected between interconnection power line 88 and terminal 67 of controller 45. The actuator side of relay 110 is shown therebelow connected in series with the solenoid coil of valve 58 which together are connected between the alternating voltage lines 82 and 83. Connected this way, controller 45 can control the draining of insertion tank 28 through tube 37, valve 58, tube 60 and a portion of tube 59 into reservoir 48. A final light, 111, is shown connected in parallel with the control side of relay 110 so that this light is illuminated on panel 31 whenever there is a draining from insertion tank 28 to reservoir 48.

The last two items shown connected in FIG. 9 are high liquid level sensor 70 and low liquid level sensor 71 used in connection with reservoir 48. Each of these are connected between alternating voltage lines 82 and 83. These connections are to provide electrical power to sensors 70 and 71 in their controlling of switches as indicated above in connection with FIG. 7.

Figure 10:
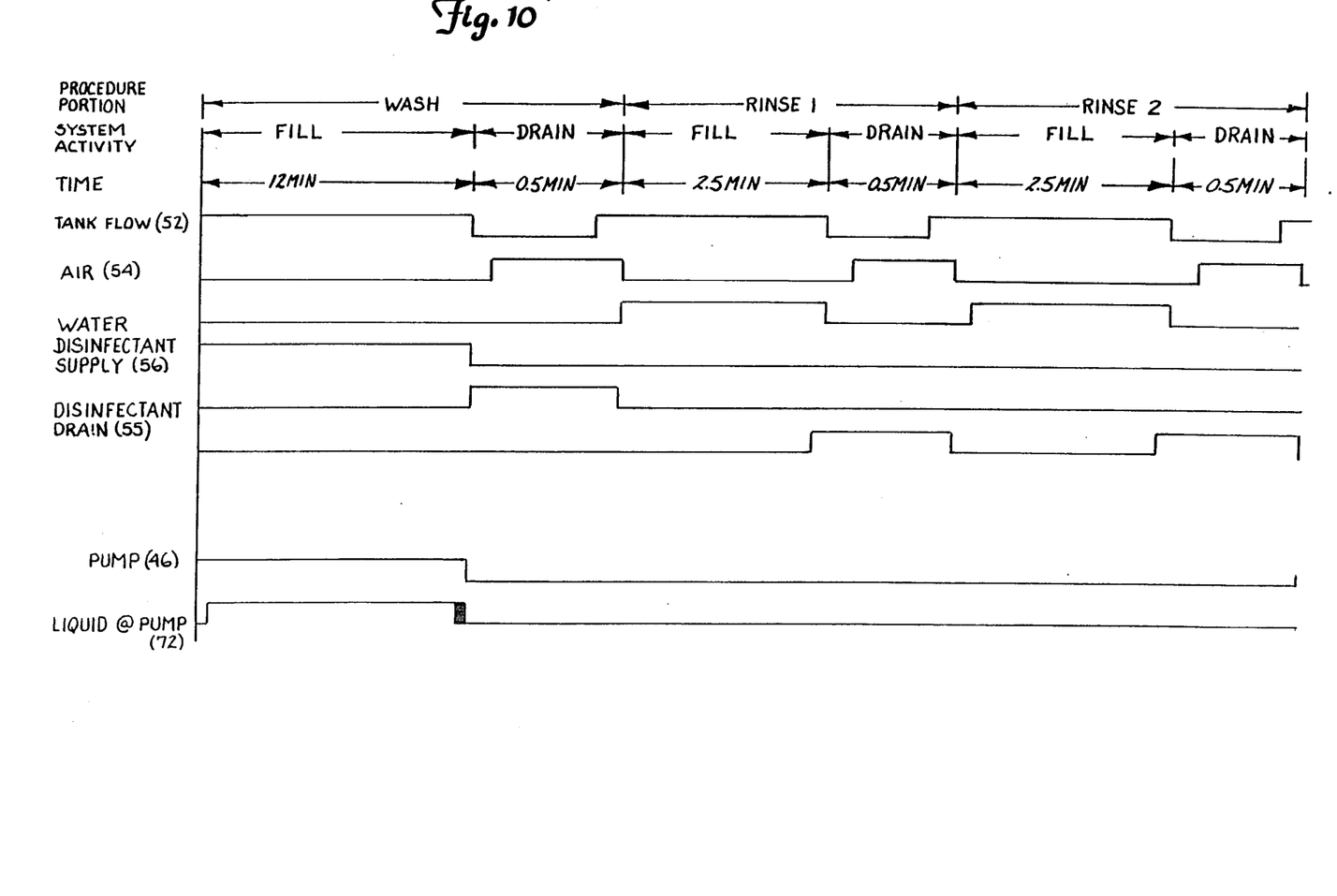
FIG. 10 shows a timing diagram illustrating a typical cleaning procedure with the present invention.

FIG. 10 shows the timing and some of the signals connected with a typical cleaning procedure in cleaning system 25. As can be seen along the top row, the procedure can be divided into a first disinfectant wash portion followed by two successive rinse portions as earlier indicated. Each of these cleaning procedure portions are indicated in the line immediately below, in FIG. 10, to be considered to be divided into a fill portion and a drain portion. Below that there is a line indicating some typical times which are used for the cleaning procedure.

A cleaning procedure starts with a manual scrubbing of the outside of endoscope 10 in a cleaning solution before it is ever mounted in cleaning machine 25. This includes inserting a brush down the passageway 21 to clear that passageway. While the remaining passageways can be checked to determine whether they will permit a liquid flow therethrough, they are typically too small to permit having a brush inserted therein.

Next, insertion portion 16 of endoscope 10 is inserted in insertion opening 27 and into container 30 to coil therein sufficiently so that control portion 15 is approximately at insertion opening 27. Tubes 41 are connected to those access orifices of passageways which are to be cleaned, typically the orifice for passageway 21 and combined orifices for passageways 19 and 17'. The remaining orifice for this passageway at this end of endoscope 10 is blocked to prevent any flows thereout.

If the endoscope has a carbon dioxide gas channel and is arranged generally in the way shown in FIG. 1, the flow therethrough by connecting a tube 41 to the access orifice of passageway 20 may result in relatively little flow therethrough because of the relatively small pressure drop therealong due to the merging of passageway 20 with passageway 17''. An alternative is to instead connect another tube, 112, to the orifice of passageway 20 and insert that tube directly into insertion tank 28 through another insertion opening, 27', in the top of cleaning system 25 as shown in FIGS. 2 and 3. The result will be that fluid forced through passageway 17" will also be forced through passageway 2 into insertion tank 28 with a substantial flow to give a good cleaning action.

Further, valves 18 and 22 and the adjacent cap on passageway 20 are removed form control portion 15 and a clamping arrangement is provided thereover. This prevents any flow out of the openings from which the valves were taken.

At this point, start button 92 is pushed to begin the cleaning procedure associated with cleaning system 25. As can be seen from FIG. 10, pump 46 immediately begins to pump disinfectant fluid being made available thereto by the opening of valve 56. That this fluid is avilable for pumping is sensed shortly afterward by pump sensor 72. Disinfectant fluid pumped by pump 46 passes through ball check valve 51 and immediately to tubes 41 and into endoscope 10 and to insertion tank 28. Valve 52 is opened to permit pump 46 to also pump disinfectant directly into tank 28. As earlier described, valve 57 opens simultaneously with valve 56 to permit overflow of disinfectant fluid reaching tube 35 to flow back to reservoir 48. In this way, a continuous flow of disinfectant fluid occurs through endoscope 10 and through insertion tank 28.

This continuous flow through and past endoscope 10 is quite important. The result is that there is no static soaking of the biological matter residues in the passageways by the disinfectant fluid, rather there is a fluid flow past or carrying along such biological matter. If the disinfectant is in a non-flow situation and soaking such biological matter, many kinds of biological matter will become quite hardened and adhere quite strongly to endoscope 10 frustrating the desire to remove same. Further, a forced flow assures continuous contact between the passageway surfaces and the disinfectant fluid. For a static soaking, gravity can pull the disinfectant away from surfaces at higher positions, or the trapping of air bubbles can prevent fluid contact with some surfaces, so that continuous fluid contact cannot be assured.

On the other hand, the continuous flow should not be at too high a velocity which could cause the disinfectant to foam or could entrain a quantity of air bubbles therein, reducing the amount of effective time that disinfectant fluid is against the endoscope structure during a wash portion of the cleaning procedure. Typically, the disinfectant fluid flow time marked "fill" in FIG. 10 will be on the order of 12 minutes, but this time is selectable and can be shortened or extended.

Several safety measures are in effect to prevent any chance of disinfectant finding its way out of insertion tank 28 other than to reservoir 48 or, when desired, to a drain. First, as already noted, there is provided a continual overflow flow path back to reservoir 48 along tube 35, through valve 57 and then along tube 59. Should there be any blockage of this path, a further increase in depth of disinfectant will bring it to overflow tube 36 and cause it to flow therethrough into the external drain system. Multiple tubes 36 are used to reduce chances of any blockage of this path. Should both of these be blocked, there is, in addition, liquid level sensor 69, which upon sensing any fluid will cause the cleaning system 25 to entirely stop operations.

At the end of this disinfectant flow time, pump 46 is turned off and valve 56 is closed. Valve 58 is opened to permit draining of the disinfectant remaining in insertion tank 28 and endoscope 10 to reservoir 48 through tube 37, valve 58, tube 60 and a poriton of tube 59. At the same time, valve 52 is closed followed shortly by the opening of valve 54 to permit compressed air to be applied to the passageways of endoscope 10 to recover the disinfectant residues therein. Then, valve 52 is reopened before valve 54 is closed to permit compressed air to flow through tube 63, valve 52 and tube 38 into insertion tank 28 to recover any disinfectant residues therealong. Recovering such disinfectant, in addition to a cost saving, reduces the amount of rinsing required in the further cleaning cycle portions to come.

Then valve 54 is closed to eliminate the flow of compressed air, and valve 58 is closed to prevent any further draining from insertion tank 28. This is followed shortly thereafter by the opening of valve 53 to permit a rinsing water flow to begin. Rinsing water, being under pressure from the water source, flows through pump 46 and ball check valve 51 to tubes 41 and into endoscope 10 and then into insertion tank 28. Valve 52, being already open, permits insertion tank 28 to be filled through tube 38. Once again, a continuous flow of rinsing water is achieved since the water will continue to flow into tank 28 through endoscope 10 and tube 38 reaching the level of tube 36 and then flowing thereout through connection 43 to cleaning system drain tube 42 and into the external drain arrangement. Note that valve 57 is closed and so there will be no rinsing water flow past valve 57.

As a result, rinsing water will be continually flowing through and passing endoscope 10 during this time, and in addition, flowing through pump 46 and the path taken by the disinfectant in reaching insertion tank 28. This is continued for approximately two and one-half minutes. Again, there is a backup to tank 28 overfilling with rinsing water due to the presence of liquid level sensor 69.

At that point, valve 52 closes while valve 55 opens to drain any rinsing water remaining in insertion tank 28 through tube 37, valve 55, tube 60, connection 44 and to cleaning system drain tube 42 to the external drain. Shortly thereafter, valve 54 opens permitting compressed air to again flow through the passageways of endoscope 10 to clear any residues out of the tubes. Again, thereafter valve 52 is opened so that the compressed air also clears out the rinsing water path into insertion tank 28. At that point, valve 55 is closed to prevent any further drainage from insertion tank 28 and shortly thereafter, valve 53 is reopened to provide a rinsing water flow for the second rinse cycle.

This second rinse cycle proceeds much as the first rinse cycle, again followed by passing compressed air through passageways of endoscope 10 and much of the disinfectant path in cleaning system 25. This removal of the rinse water minimizes any dilution by having such rinse water get into the disinfectant fluid in the next cleaning procedure undertaken with cleaning system 25. Of course, a compressed air purge also, in removing most water from endoscope 10, prevents such water from spilling when endoscope 10 is removed from cleaning system 25 after completion of the cleaning procedure therein.

Although the present invention has been described with reference to preferred embodiments, workers skilled in the art will recognize that changes may be made in form and detail without departing from the spirit and scope of the invention.

What is claimed is:

1. A cleaning system for cleaning at least that portion of a flexible, elongated object having at least one internal passageway therein extending along its length which passageway terminates at a corresponding terminal orifice at an orifice end of said object portion and at a corresponding access orifice at that end remaining of said object portion which occurs at an access location along said object, said system comprising:

an insertion tank capable of storing a fluid and having an object insertion opening through which it is capable of receiving therein said orifice end of said object portion, said insertion tank further having therein an open container means rotatably mounted in said insertion tank at a support side of said open container means opposite a reception opening to said container means such that said object portion, if its orifice end is entered in said object insertion opening, can continue into said open container means through said reception opening therein and flexibly bend to have its orifice end and selected other parts thereof contained in said open container means with said object having its remainder extending through said object insertion opening and outside of said insertion tank including said access orifice;

a first fluid control valve means to selectively allow fluids to pass therethrough;

a fluid transfer means connected to said first fluid control valve means to permit transfers of fluids passing through said first fluid control valve means; and an object access connection means adapted for connection to said access orifice of said object to permit fluid transfers thereto, said first fluid control valve means and said fluid transfer means, connected together as aforesaid, being between said object access means and a first connection means adapted for connection to a source of a first fluid such that said object access connection can accept any of said first fluid permitted to pass by said first fluid control valve means.

2. The apparatus of claim 1 wherein said first connection means is connected to a reservoir for containing said first fluid as a source thereof, said fluid transfer means comprising a pump means for pumping said first fluid to said object access connection.

3. The apparatus of claim 2 wherein there is provided a second fluid control valve means to selectively allow fluids to pass therethrough and which is connected to an insertion tank drain interconnection means to permit fluid transfers from said insertion tank to said second fluid control valve means, said reservoir being accessible to said second fluid control valve means to accept any fluids passed therethrough.

4. The apparatus of claim 3 wherein there is provided a third fluid control valve means to selectively allow fluids to pass therethrough, and there is further provided an overflow interconnection which is connected between said insertion tank, at a selected distance from said insertion tank drain interconnection means, and said third fluid control valve means to permit fluid transfers from said insertion tank to said third fluid control valve means, said reservoir being accessible to said third fluid control valve means to accept any fluids passed therethrough.

5. The apparatus of claim 2 wherein a heating means is provided for heating said reservoir.

6. The apparatus of claim 2 wherein there is further provided a second fluid control valve means to selectively allow fluids to pass therethrough and which is adapted for connection to a source of a second fluid to permit transfer of said second fluid thereto, said object access connector means also being connected to said second fluid control valve means to accept any fluids passed therethrough.

7. The apparatus of claim 2 wherein there is further provided a second fluid control valve means to selectively allow fluids to pass therethrough, said fluid supply transfer interconnection means also connected to said second fluid control valve means to permit fluid transfers thereto, and said insertion tank is connected to said second fluid control valve means to accept any fluid transfers passed therethrough.

8. The apparatus of claim 2 wherein there is provided a second fluid control valve means to selectively allow fluids to pass therethrough and which is connected to an insertion tank drain interconnection means to permit fluid transfers from said insertion tank to said second fluid control valve means, and there is further provided a drain transfer interconnection means, adapted for providing transfers to a waste disposal means, said drain transfer interconnection means being connected to said second fluid control valve means to accept any fluids passed therethrough.

9. The apparatus of claim 8 wherein there is provided an overflow interconnection which is connected between said insertion tank, at a selected distance from said insertion tank drain interconnection means, and said drain transfer interconnection means to permit fluid transfers from said insertion tank to said drain transfer interconnection means.

10. The apparatus of claim 2 wherein there is provided a second fluid control valve means to selectively allow fluids to pass therethrough and which is connected to said fluid transfer means to permit transfer of fluids passing through said second fluid control valve means, said second fluid control valve means also being connected to a second connection means adapted for connection to a source of a second fluid.

11. The apparatus of claim 1 wherein there is further provided a second fluid control valve means to selectively allow fluids to pass therethrough and which is adapted for connection to a source of a second fluid to permit transfer of said second fluid thereto, said object access connector means also being connected to said second fluid control valve means to accept any fluids passed therethrough.

12. The apparatus of claim 11 wherein there is further provided a third fluid control valve means to selectively allow fluids to pass therethrough, said fluid supply transfer interconnection means also connected to said third fluid control valve means to permit fluid transfers thereto, and said insertion tank is connected to said third fluid control valve means to accept any fluid transfers passed therethrough.

13. The apparatus of claim 11 wherein there is provided a third fluid control valve means to selectively allow fluids to pass therethrough and which is connected to an insertion tank drain interconnection means to permit fluid transfers from said insertion tank to said third fluid control valve means, and there is further provided a drain transfer interconnection means, adapted for providing transfers to a waste disposal means, said drain transfer interconnection means being connected to said third fluid control valve means to accept any fluids passed therethrough.

14. The apparatus of claim 13 wherein there is provided an overflow interconnection which is connected between said insertion tank, at a selected distance from said insertion tank drain interconnection means, and said drain transfer interconnection means to permit fluid transfers from said insertion tank to said drain transfer interconnection means.

15. The apparatus of claim 11 wherein a heating means is provided to heat said first fluid before it reaches said first fluid control valve means.

16. The apparatus of claim 1 wherein there is further provided a second fluid control valve means to selectively allow fluids to pass therethrough, said fluid transfer means and said first fluid control valve means, connected together as aforesaid, being connected between said second fluid control valve means and said first connection means such that said second fluid control valve means can receive that said first fluid permitted to pass by said first fluid control valve means, and said insertion tank being connected to said second fluid control valve means to accept any fluid transfers passed therethrough.

17. The apparatus of claim 16 wherein there is provided a third fluid control valve means to selectively allow fluids to pass therethrough and which is connected to an insertion tank drain interconnection means to permit fluid transfers from said insertion tank to said third fluid control valve means, and there is further provided a drain transfer interconnection means adapted for providing transfers to a waste disposal means, said drain transfer interconnection means being connected to said third fluid control valve means to accept any fluids passed therethrough.

18. The apparatus of claim 17 wherein there is provided an overflow interconnection which is connected between said insertion tank, at a selected distance from said insertion tank drain interconnection means, and said drain transfer interconnection means to permit fluid transfers from said insertion tank to said drain transfer interconnection means.

19. The apparatus of claim 1 wherein a heating means is provided to heat said first fluid before it reaches said first fluid control valve means.

20. The apparatus of claim 1 wherein there is provided a second fluid control valve means to selectively allow fluids to pass therethrough and which is connected to an insertion tank drain interconnection means to permit fluid transfers from said insertion tank to said second fluid control valve means, and there is further provided a drain transfer interconnection means, adapted for providing fluid transfers to a waste disposal means, said drain transfer interconnection means being connected to said second fluid control valve means to accept any fluids passed therethrough.

21. The apparatus of claim 20 wherein there is provided an overflow interconnection which is connected between said insertion tank, at a selected distance from said insertion tank drain interconnection means, and said drain transfer interconnection means to permit fluid transfers from said insertion tank to said drain transfer interconnection means.

* * * * *